United States Patent
Gao et al.

(10) Patent No.: US 7,604,615 B2
(45) Date of Patent: *Oct. 20, 2009

(54) SURGICAL CASSETTE WITH BUBBLE SEPARATING STRUCTURE

(75) Inventors: Shawn X. Gao, Irvine, CA (US); David M. Domash, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/384,702

(22) Filed: Mar. 20, 2006

(65) Prior Publication Data

US 2007/0219494 A1    Sep. 20, 2007

(51) Int. Cl.
*A61M 1/00* (2006.01)
*A61F 9/007* (2006.01)

(52) U.S. Cl. ...................................... 604/122; 607/107

(58) Field of Classification Search ................. 604/122, 604/35, 118, 403, 131, 19; 417/477.2; 607/107
See application file for complete search history.

(56) References Cited

U.S. PATENT DOCUMENTS

| | | | |
|---|---|---|---|
| 3,683,913 A | | 8/1972 | Kurtz et al. |
| 3,920,014 A | * | 11/1975 | Banko ........................ 604/31 |
| 3,963,027 A | * | 6/1976 | Muriot ....................... 604/120 |
| 4,007,742 A | * | 2/1977 | Banko ........................ 604/31 |
| 4,019,514 A | * | 4/1977 | Banko ........................ 604/31 |
| 4,052,987 A | * | 10/1977 | Wuchinich et al. ............ 604/65 |
| 4,274,411 A | * | 6/1981 | Dotson, Jr. .................... 604/30 |
| 4,429,693 A | * | 2/1984 | Blake et al. ................. 604/133 |
| 4,661,093 A | * | 4/1987 | Beck et al. .................. 604/543 |
| 4,758,238 A | | 7/1988 | Sundblom et al. |
| 4,863,452 A | * | 9/1989 | Irmiter et al. ............... 604/408 |
| 4,935,005 A | * | 6/1990 | Haines ........................ 604/30 |
| 4,963,131 A | * | 10/1990 | Wortrich ...................... 604/34 |
| 5,039,280 A | * | 8/1991 | Saulgeot et al. ............. 417/205 |
| 5,041,096 A | | 8/1991 | Beuchat et al. |
| 5,106,366 A | | 4/1992 | Steppe |
| 5,125,891 A | * | 6/1992 | Hossain et al. ................ 604/34 |
| 5,163,900 A | * | 11/1992 | Wortrich ...................... 604/30 |
| 5,195,960 A | * | 3/1993 | Hossain et al. ................ 604/34 |
| 5,267,956 A | | 12/1993 | Beuchat |
| 5,364,342 A | | 11/1994 | Beuchat et al. |
| 5,582,601 A | | 12/1996 | Wortrich et al. |
| 5,676,650 A | * | 10/1997 | Grieshaber et al. ............ 604/28 |
| 5,747,824 A | * | 5/1998 | Jung et al. ................... 250/577 |
| 5,897,524 A | * | 4/1999 | Wortrich et al. ............... 604/30 |
| 5,904,669 A | * | 5/1999 | Schildgen et al. ............ 604/246 |
| 6,251,113 B1 | * | 6/2001 | Appelbaum et al. ......... 606/107 |
| 6,261,283 B1 | | 7/2001 | Morgan et al. |
| 6,290,690 B1 | * | 9/2001 | Huculak et al. .............. 604/521 |
| 6,293,926 B1 | | 9/2001 | Sorensen et al. |
| 6,319,223 B1 | * | 11/2001 | Wortrich et al. ............... 604/30 |
| 6,425,883 B1 | * | 7/2002 | Urich et al. .................. 604/119 |
| 6,478,781 B1 | * | 11/2002 | Urich et al. .................. 604/264 |

(Continued)

FOREIGN PATENT DOCUMENTS

WO    9605873 A1    2/1996

*Primary Examiner*—Kevin C Sirmons
*Assistant Examiner*—Michael J Anderson
(74) *Attorney, Agent, or Firm*—W. David Lee

(57) ABSTRACT

A surgical cassette having an aspiration chamber with a bubble separating structure. The bubble separating structure facilitates accurate, reliable measurement of the fluid level in the chamber.

6 Claims, 3 Drawing Sheets

U.S. PATENT DOCUMENTS

| | | |
|---|---|---|
| 6,511,454 B1 * | 1/2003 | Nakao et al. .................. 604/31 |
| 6,561,999 B1 | 5/2003 | Nazarifar et al. |
| 6,572,349 B2 | 6/2003 | Sorensen et al. |
| 6,579,255 B2 * | 6/2003 | Kadziauskas et al. ......... 604/35 |
| 6,632,214 B2 * | 10/2003 | Morgan et al. .............. 604/540 |
| 6,740,074 B2 | 5/2004 | Morgan et al. |
| 6,824,525 B2 * | 11/2004 | Nazarifar et al. ............. 604/30 |
| 6,908,451 B2 * | 6/2005 | Brody et al. ................. 604/118 |
| 6,962,488 B2 | 11/2005 | Davis et al. |
| 7,175,606 B2 * | 2/2007 | Bowman et al. ............. 604/29 |
| 2007/0005029 A1 * | 1/2007 | Hopkins et al. ............. 604/317 |
| 2007/0005030 A1 * | 1/2007 | Hopkins et al. ............. 604/317 |
| 2007/0049898 A1 * | 3/2007 | Hopkins et al. ............. 604/403 |
| 2007/0073234 A1 * | 3/2007 | Nazarifar et al. ............ 604/151 |

* cited by examiner

SURGICAL CASSETTE WITH BUBBLE SEPARATING STRUCTURE

FIELD OF THE INVENTION

The present invention generally pertains to a surgical cassette for use with microsurgical systems, and more particularly to such cassettes for use with ophthalmic microsurgical systems.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. The types of aspiration systems used, prior to the present invention, were generally characterized as either flow controlled or vacuum controlled, depending upon the type of pump used in the system. Each type of system has certain advantages.

Vacuum controlled aspiration systems are operated by setting a desired vacuum level, which the system seeks to maintain. Flow rate is dependent on intraocular pressure, vacuum level, and resistance to flow in the fluid path. Actual flow rate information is unavailable. Vacuum controlled aspiration systems typically use a venturi or diaphragm pump. Vacuum controlled aspiration systems offer the advantages of quick response times, control of decreasing vacuum levels, and good fluidic performance while aspirating air, such as during an air/fluid exchange procedure. Disadvantages of such systems are the lack of flow information resulting in transient high flows during phacoemulsification or fragmentation coupled with a lack of occlusion detection. Vacuum controlled systems are difficult to operate in a flow controlled mode because of the problems of non-invasively measuring flow in real time.

Flow controlled aspiration systems are operated by setting a desired aspiration flow rate for the system to maintain. Flow controlled aspiration systems typically use a peristaltic, scroll, or vane pump. Flow controlled aspiration systems offer the advantages of stable flow rates and automatically increasing vacuum levels under occlusion. Disadvantages of such systems are relatively slow response times, undesired occlusion break responses when large compliant components are used, and vacuum can not be linearly decreased during tip occlusion. Flow controlled systems are difficult to operate in a vacuum controlled mode because time delays in measuring vacuum can cause instability in the control loop, reducing dynamic performance.

One currently available ophthalmic surgical system, the MILLENIUM system from Storz Instrument Company, contains both a vacuum controlled aspiration system (using a venturi pump) and a separate flow controlled aspiration system (using a scroll pump). The two pumps can not be used simultaneously, and each pump requires separate aspiration tubing and cassette.

Another currently available ophthalmic surgical system, the ACCURUS® system from Alcon Laboratories, Inc., contains both a venturi pump and a peristaltic pump that operate in series. The venturi pump aspirates material from the surgical site to a small collection chamber. The peristaltic pump pumps the aspirate from the small collection chamber to a larger collection bag. The peristaltic pump does not provide aspiration vacuum to the surgical site. Thus, the system operates as a vacuum controlled system.

In both vacuum controlled aspiration systems and flow controlled aspiration systems, the liquid infusion fluid and ophthalmic tissue aspirated from the surgical site are directed into an aspiration chamber within a surgical cassette. In certain vacuum controlled aspiration systems, it is important to have an accurate measurement of the level of liquid in the aspiration chamber. Such accurate measurement has proved challenging in conventional aspiration systems for several reasons. In many conventional cassettes, aspirated fluid enters an aspiration chamber from the top of the chamber. Such entry creates a drip into the chamber resulting in a fluid level disturbance and difficulties in measuring the fluid level. Optical sensors have been used to measure the fluid level in aspiration chambers. However, precise measurements of such fluid levels with optical sensors has proven difficult, and optical sensors are sensitive to disturbances from ambient light entering into the cassette.

Accordingly, a need continues to exist for an improved method of measuring the fluid level within the aspiration chamber of a surgical cassette.

SUMMARY OF THE INVENTION

The present invention relates to a surgical cassette having an aspiration chamber disposed therein. The aspiration chamber includes a first entry for fluidly coupling to a surgical device, a second entry for fluidly coupling to a source of vacuum in a surgical console for aspirating liquid infusion fluid from the surgical device, and a bubble separating structure that divides the aspiration chamber into a first section and a second section. The bubble separating structure has a first opening that allows passage of liquid but prevents passage of air bubbles from the first section to the second section, and a second opening that allows liquid from the second section to return to the first section.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
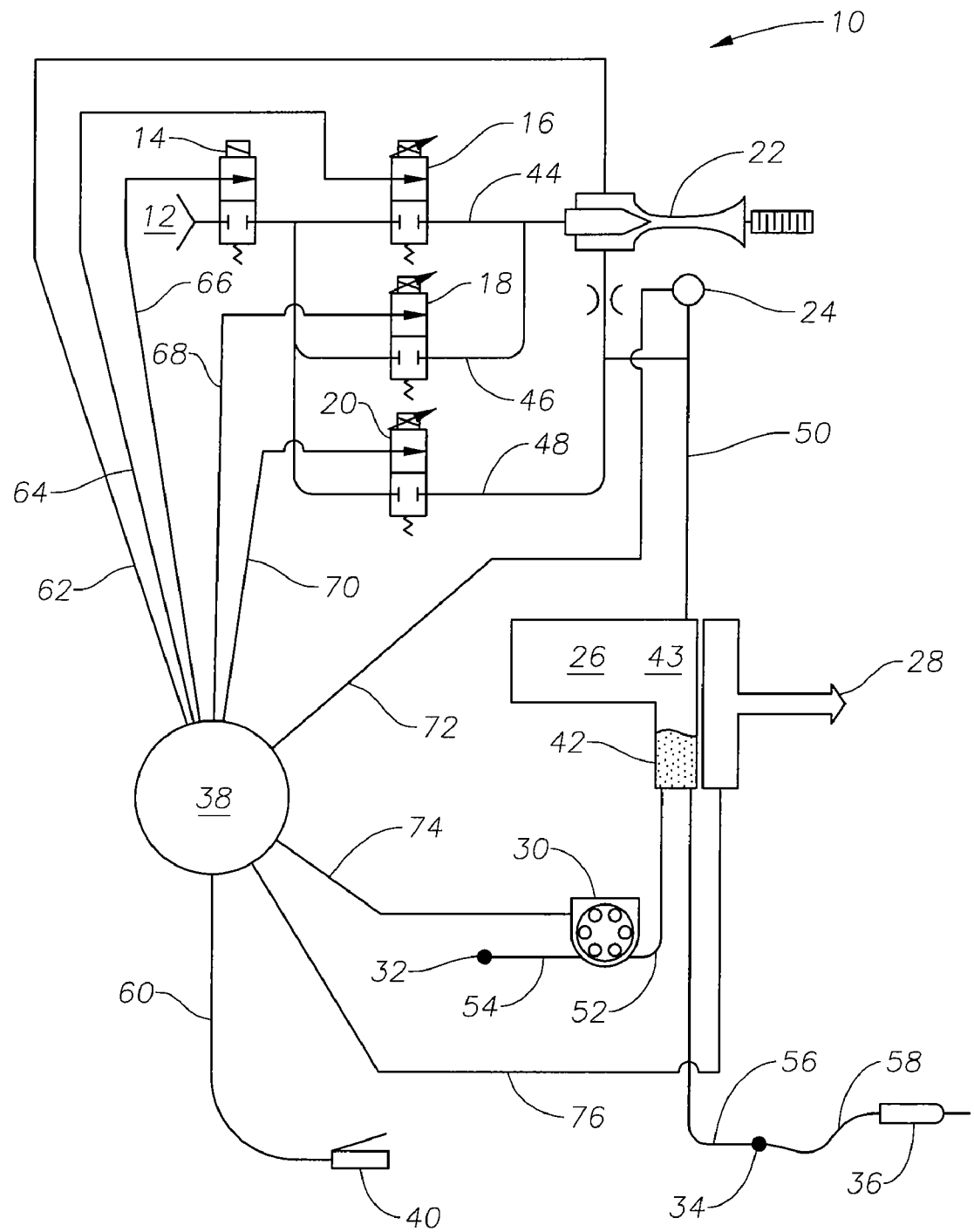
FIG. 1 is a schematic diagram illustrating aspiration control in a microsurgical system.
Figure 2:
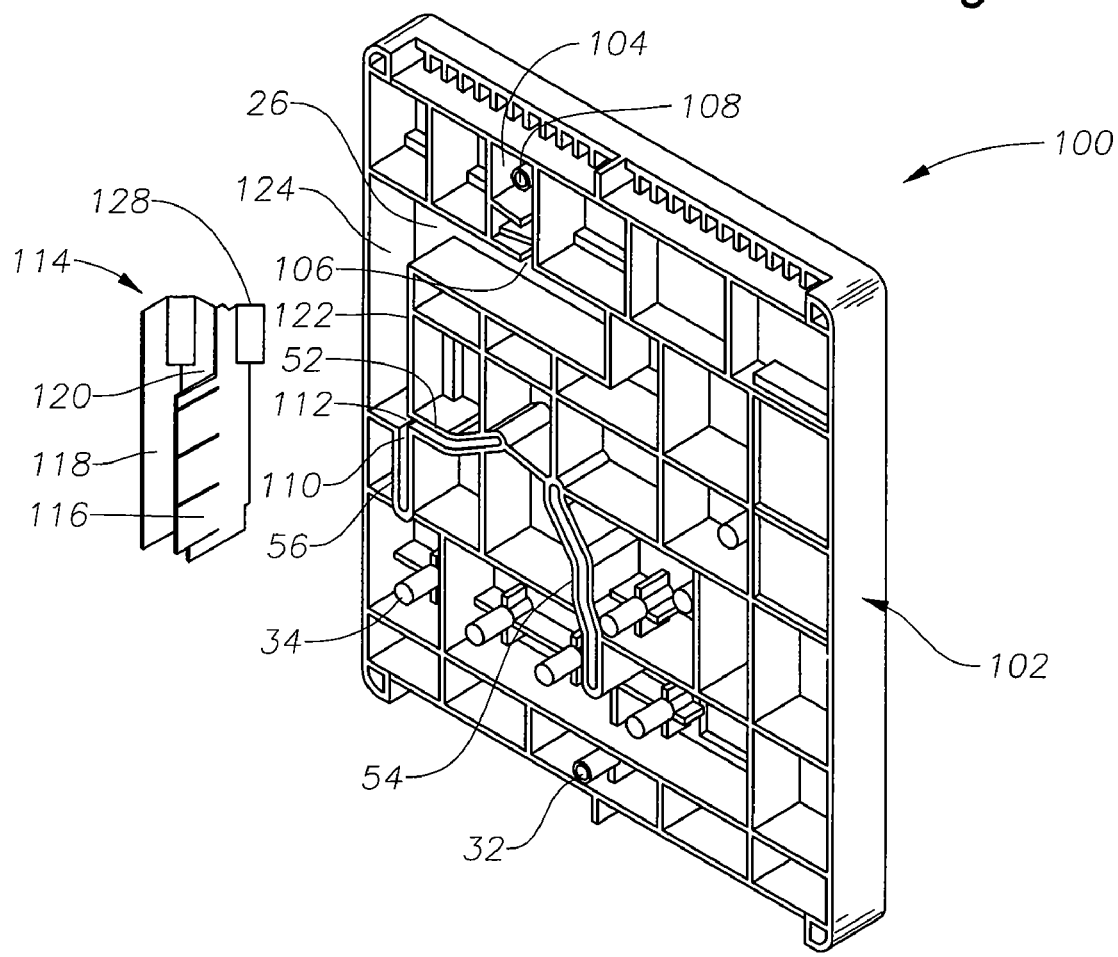
FIG. 2 is a front, perspective, exploded view of a body of a surgical cassette and a bubble separating structure according to a preferred embodiment of the present invention.
Figure 3:
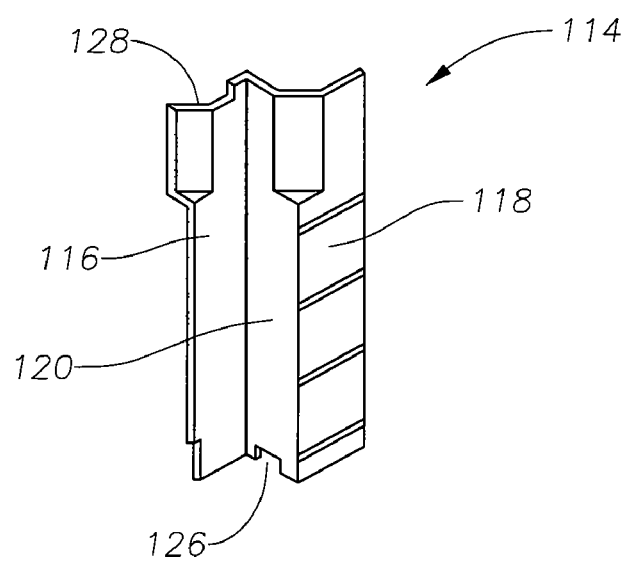
FIG. 3 is a rear, perspective, slightly enlarged view of the bubble separating structure of FIG. 2.
Figure 5:
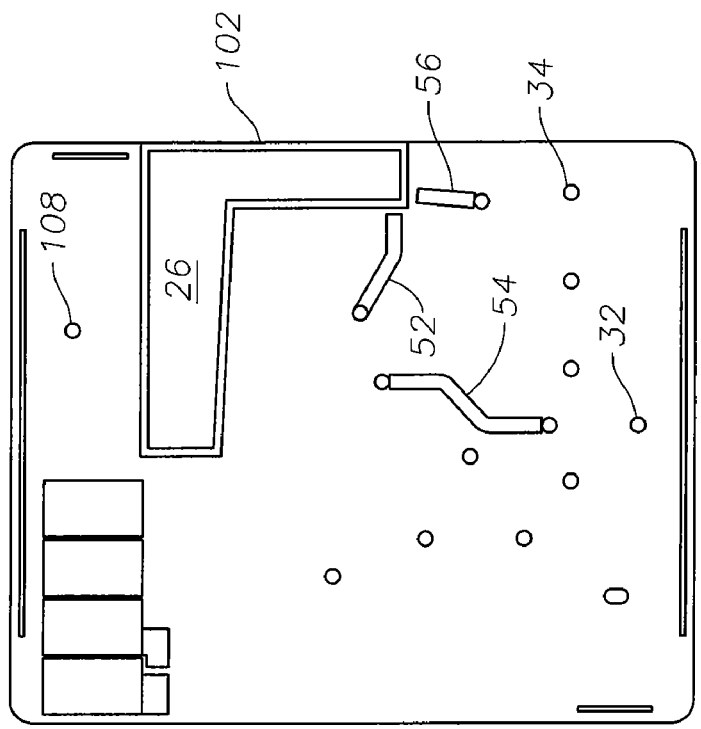
FIG. 5 is a rear view of the surgical cassette body of FIG. 2.
Figure 4:
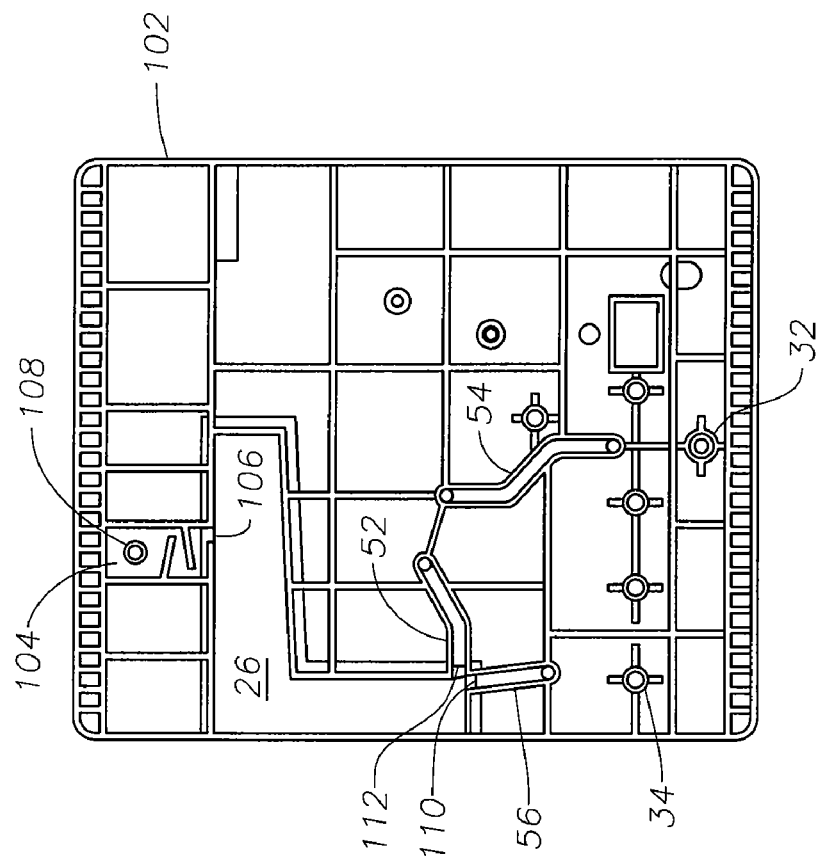
FIG. 4 is a front view of the surgical cassette body of FIG. 2.

The preferred embodiments of the present invention and their advantages are best understood by referring to FIGS. 1-5 of the drawings, like numerals being used for like and corresponding parts of the various drawings.

Microsurgical system 10 includes a pressurized gas source 12, an isolation valve 14, a vacuum proportional valve 16, an optional second vacuum proportional valve 18, a pressure proportional valve 20, a vacuum generator 22, a pressure transducer 24, an aspiration chamber 26, a fluid level sensor 28, a pump 30, a collection bag 32, an aspiration port 34, a surgical device 36, a computer or microprocessor 38, and a proportional control device 40. The various components of system 10 are fluidly coupled via fluid lines 44, 46, 48, 50, 52, 54, 56, and 58. The various components of system 10 are electrically coupled via interfaces 60, 62, 64, 66, 68, 70, 72, 74, and 76. Valve 14 is preferably an "on/off" solenoid valve. Valves 16-20 are preferably proportional solenoid valves. Vacuum generator 22 may be any suitable device for generating vacuum but is preferably a vacuum chip or a venturi chip that generates vacuum when isolation valve 14 and vacuum proportional valves 16 and/or 18 are open and gas from pressurized gas source 12 is passed through vacuum generator 22. Pressure transducer 24 may be any suitable device for directly or indirectly measuring pressure and vacuum. Fluid level sensor 28 may be any suitable device for measuring the level of a fluid 42 within aspiration chamber 26 but is preferably capable of measuring fluid levels in a continuous manner. Fluid level sensor 28 is most preferably an optical sensor capable of measuring fluid levels in a continuous manner. Pump 30 may be any suitable device for generating vacuum but is preferably a peristaltic pump, a scroll pump, or a vane pump. Microprocessor 38 is capable of implementing feedback control, and preferably PID control. Proportional controller 40 may be any suitable device for proportionally controlling system 10 and/or surgical device 36 but is preferably a foot controller.

System 10 preferably utilizes three distinct methods of controlling aspiration, vacuum control, suction control, and flow control. These methods are more fully described in co-pending U.S. application Ser. No. 11/158,238 filed Jun. 21, 2005 and co-pending U.S. application Ser. No. 11/158,259, both of which are commonly owned with the subject application and are incorporated herein by reference.

In each of these methods, vacuum may be provided to surgical device 36 and aspiration chamber 26 via fluid lines 50, 56, and 58. Aspiration chamber 26 fills with fluid 42 aspirated by surgical device 36. Fluid 42 includes liquid infusion fluid as well as aspirated ophthalmic tissue.

As shown in FIGS. 2-5, a surgical cassette 100 has a body 102 including aspiration chamber 26 and an aspiration source chamber 104. A cover, which is fluidly sealed to the front side of body 102, is not shown for purposes of clarity. A pinch plate, which is fluidly sealed to the rear side of body 102, is not shown for purposes of clarity. Aspiration source chamber 104 preferably has a small volume relative to aspiration chamber 26. An entry 106 fluidly couples aspiration chamber 26 and aspiration source chamber 104. A port 108 fluidly couples aspiration source chamber 104 and fluid line 50. As discussed hereinabove, fluid line 50 is fluidly coupled to vacuum generator 22. An entry 110 fluidly couples aspiration chamber 26 and fluid line 56. As discussed hereinabove, fluid line 56 is fluidly coupled to surgical device 36 via port 34 and fluid line 58. An entry 112 fluidly couples aspiration chamber 26 and fluid line 52. A bubble separating structure 114 is disposed within aspiration chamber 26. Bubble separating structure 114 preferably includes a first support surface 116 for mating with an internal wall 122 of aspiration chamber 26, a second support surface 118 for mating with an internal wall 124 of aspiration chamber 26, and a dividing surface 120 disposed between first support surface 116 and second support surface 118. Dividing surface 120 has an opening 126 disposed at or near its lower end, and support surface 116 has an opening 128 at or near its top end. Body 102 is preferably molded from a plastic material. Aspiration chamber 26, aspiration source chamber 104, entry 106, port 108, entry 110, and entry 112 are preferably integrally molded into body 102. Bubble separating structure 114 is preferably molded from a plastic material and is designed to be frictionally secured within aspiration chamber 26. Alternatively, bubble separating structure 114 may be integrally molded into body 102 as well. In either case, bubble separating structure 114 is preferably opaque.

As shown best in FIG. 1, liquid 42 is present in aspiration chamber 26, and air 43 is present in aspiration chamber 26 above liquid 42. When the surgical system supplies vacuum to aspiration chamber 26, some liquid 42 is mixed with air 43, typically on or in air bubbles. Bubble separating structure 114 separates aspiration chamber 26 into front and rear sections. Fluid level sensor 28 measures the fluid level in the rear section of aspiration chamber 26 behind dividing surface 120. As the liquid/air mixture enters aspiration chamber 26 via entry 110, opening 126 of dividing surface 120 blocks the passage of air bubbles and allows only liquid to pass into the rear section of aspiration chamber 26. Opening 128 of support surface 116 allows the liquid in the rear section of aspiration chamber 20 to re-enter the front section of aspiration chamber 26. The level of fluid 42 in aspiration chamber 26 remains equal on both sides of bubble separating structure 114. By separating air bubbles into the front section of aspiration chamber 26, bubble separating structure 114 allows fluid level sensor 28 to measure the level of fluid in aspiration chamber 26 in an accurate, reliable manner and eliminates any errors associated with air bubbles. The opaque nature of bubble separating structure 114 eliminates any errors of fluid sensor 28 associated with ambient light entering into cassette 100.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A surgical cassette, comprising:
    an aspiration chamber, comprising:
        a first entry for fluidly coupling to a surgical device;
        a second entry for fluidly coupling to a source of vacuum in a surgical console for aspirating liquid infusion fluid from said surgical device; and
        a bubble separating structure disposed within said aspiration chamber that divides said aspiration chamber into a first section and a second section, said bubble separating structure having:
            a first support surface for mating with a first internal wall of said aspiration chamber;
            a second support surface for mating with a second internal wall of said aspiration chamber; and
            a dividing surface disposed between said first support surface and said second support surface;
        wherein said dividing surface has a first opening that allows passage of liquid but prevents passage of air bubbles from said first section to said second section, said first support surface has a second opening that allows liquid from said second section to return to said first section, and said second section collects fluid for measuring a fluid level in said aspiration chamber.

2. The surgical cassette of claim 1 wherein said first entry is disposed proximate a bottom of said aspiration chamber and said second entry is disposed proximate a top of said aspiration chamber.

3. The surgical cassette of claim 2 wherein said first opening is disposed proximate a bottom of said dividing surface.

4. The surgical cassette of claim 3 wherein said second opening is disposed proximate a top of said first support surface.

5. The surgical cassette of claim 4 wherein said first opening and said second opening function to keep a fluid level in said first section equal to a fluid level in said second section.

6. The surgical cassette of claim 1 wherein said bubble separating structure is opaque.

* * * * *